United States Patent
Nie et al.

(10) Patent No.: US 10,615,624 B2
(45) Date of Patent: Apr. 7, 2020

(54) WIRELESS CHARGING METHOD AND APPARATUS BASED ON RADIO FREQUENCY RECEIVING AND PHASE COMPENSATION RETRANSMISSION

(71) Applicant: UNIVERSITY OF ELECTRONIC SCIENCE AND TECHNOLOGY OF CHINA, Chengdu (CN)

(72) Inventors: Zaiping Nie, Chengdu (CN); Yuan Yang, Chengdu (CN); Xianzheng Zong, Chengdu (CN)

(73) Assignee: UNIV. OF ELECTRONIC SCIENCE AND TECH. OF CHINA, Chengdu (CN)

(*) Notice: Subject to any disclaimer, the term of this patent is extended or adjusted under 35 U.S.C. 154(b) by 347 days.

(21) Appl. No.: 15/387,813

(22) Filed: Dec. 22, 2016

(65) Prior Publication Data
US 2017/0294796 A1 Oct. 12, 2017

(30) Foreign Application Priority Data
Apr. 8, 2016 (CN) .......................... 2016 1 0218755

(51) Int. Cl.
*H02J 7/02* (2016.01)
*A61N 1/378* (2006.01)
(Continued)

(52) U.S. Cl.
CPC ............ *H02J 7/025* (2013.01); *A61N 1/3787* (2013.01); *H02J 50/23* (2016.02); *H02J 50/27* (2016.02); *H02J 50/40* (2016.02)

(58) Field of Classification Search
CPC .. H02J 7/025; H02J 50/23; H02J 50/27; H02J 50/40; A61N 1/3787
(Continued)

(56) References Cited

U.S. PATENT DOCUMENTS

| | | | |
|---|---|---|---|
| 10,038,332 B1* | 7/2018 | Leabman | H02J 7/025 |
| 2006/0169292 A1* | 8/2006 | Iddan | A61B 1/041 |
| | | | 128/899 |

(Continued)

OTHER PUBLICATIONS

Balanis, "Antenna Theory Third Edition Analysis and Design", published by John Wiley & Sons, Inc., Hoboken, New Jersey, , 2005, pp. 283-293.

(Continued)

*Primary Examiner* — Richard Isla
*Assistant Examiner* — Manuel Hernandez
(74) *Attorney, Agent, or Firm* — Potomac Law Group, PLLC

(57) ABSTRACT

Embodiments provide focused wireless charging method and apparatus based on radio frequency receiving and phase compensation retransmission. The method is based on the reciprocity principle, making each charging signal transmitted by the external charging system could stack in-phase when arriving at the embedded rechargeable battery, realizing wireless near field focusing in any given area in an unknown complex inhomogeneous propagation environment and a high charging efficiency. The focused wireless charging technology based on radio frequency receiving and phase compensation retransmission in embodiments could realize in-phase stacking and precise focus of each wireless charging signal of the external system on the embedded batteries to be charged automatically under different propagation environment, different environment medium, and possible random offset of the rechargeable battery. This method has strong environmental adaptability, high energy transmission efficiency, transmission stability, less radiation to human body and no need of accurate information of the location of charging equipment.

6 Claims, 4 Drawing Sheets

(51) Int. Cl.
*H02J 50/23* (2016.01)
*H02J 50/27* (2016.01)
*H02J 50/40* (2016.01)

(58) Field of Classification Search
USPC .......................................... 320/108; 307/104
See application file for complete search history.

(56) References Cited

U.S. PATENT DOCUMENTS

| | | | | |
|---|---|---|---|---|
| 2011/0115891 | A1* | 5/2011 | Trusty | A61B 1/00016 |
| | | | | 348/65 |
| 2012/0274154 | A1* | 11/2012 | DeLuca | H02J 17/00 |
| | | | | 307/149 |
| 2016/0049824 | A1* | 2/2016 | Stein | H04W 4/70 |
| | | | | 320/108 |

OTHER PUBLICATIONS

Deflaviis et al., "Multi-Antenna Systems for MIMO Communications", Morgan&Claypool Publishers, 2008, pp. 7-8.

* cited by examiner

WIRELESS CHARGING METHOD AND APPARATUS BASED ON RADIO FREQUENCY RECEIVING AND PHASE COMPENSATION RETRANSMISSION

FIELD OF THE INVENTION

The present invention relates to wireless charging technology, more particularly, to focused wireless charging technology based on the reciprocity relationship in complex multipath propagation environment.

BACKGROUND OF THE INVENTION

Nowadays, various types of electronic equipment (such as various types of sensors or wireless network nodes) require periodic or continuous wireless charging, because of being implanted in body in advance (including fixed type, such as cardiac pacemaker, and dynamic type, such as capsule endoscopy), or being erected in environment without power supply condition or complicated environment, or not being able to replace batteries because of the requirement of secret installation. However, in wireless charging technology, to ensure a battery to be charged could receive electromagnetic energy effectively, radio wave emitted by wireless charging equipment should have sufficient strength in the area where the battery to be charged is located. But if the wireless charging equipment emits non focused radio wave, a lot of electromagnetic wave energy could not be received by the battery to be charged and would become invalid radiation, not only resulting in the waste of energy, but also causing electromagnetic pollution to human and the surrounding environment. Thus, the goal of wireless charging technology is to realize favorable electromagnetic power focusing in area near the device to be charged by radio waves emitted by charging device.

However, as an electromagnetic emission apparatus of a wireless charging device, spot focused multiple antennas system face the following rigorous challenges when designed.

1. The difficulty of the spot electromagnetic focusing in complex or even unknown and time-varying inhomogeneous propagation environment. Usually, there is highly complex or even unknown and time-varying inhomogeneous environment between the charging equipment and the battery to be charged, leading to the highly unreasonable power distribution of the electromagnetic waves emitted by the charging device, and most of the electromagnetic waves become useless power and lead to electromagnetic pollution. It is highly unrealistic to master the actual inhomogeneous propagation environment in advance and then conduct the electromagnetic focusing design contrapuntally, because the randomness of the propagation medium (such as people's height and body shape), the time-varying characteristics (such as the movement of capsule endoscopes in digestive tract), and the complex multipath propagation effect are difficult to forecast and even harder to accurately grasp. For example, the heterogeneity of lush vegetation has random and time-varying characteristic. As another example, for the wireless charging to the electronic equipment (such as pacemaker and capsule endoscopes) embedded in body, due to the complex nonuniformity within the human body, such as people's height and body shape, breathing habits, ups and downs of the chests when breathing, the movement of the capsule endoscopes in digestive tract, the electromagnetic propagation environment present significant complex non-uniformity and random time-varying characteristic.

2. The battery to be charged is difficult to be found and precisely located, resulting in the difficulty of confirming the focused area in real time. In many applications of wireless charging, the position of the battery to be charged is difficult to be found and precisely located, even changes irregularly. So that the electromagnetic focused area could not be located. Such as the apparatus which is installed secretly, implantable, camouflaged, or installed in the pit, underwater, underground, and the apparatus covered by vegetation and in continually moving and so on.

In contrast, the existing wireless charging technology, including the charging technology based on near field coupling, and the charging technology based on electromagnetic propagation, either does not consider the electromagnetic focusing, or attempts to focus based on the pre-determined simplified propagation model, without reality and practicality; it is even not possible to realize accurate electromagnetic focusing without grasping the accurate position of the battery to be charged and the current non-uniform propagation conditions.

A new wireless energy transfer system, as a typical representation of existing technology, is disclosed in Mid-field Wireless Power Transfer for Bioelectronics by Ada S. Y. Poon in IEEE Circuits and Systems. Though this design could change the direction of energy transmission by adjusting the phase of feeding unit, it could not point to the position of electronic devices implanted in body accurately, leading to a decrease in transmission efficiency, and pollution is caused by the electromagnetic power which is not received by receiving antenna, and most of the electromagnetic power would be absorbed by body tissue, elevating the temperature of local tissue, even endangering human safety and health.

Therefore, this system needs further improvement in the application of wireless energy transferring to the device implanted in body.

SUMMARY OF THE INVENTION

For the above deficiency of the existing technology, the present invention proposes a focused wireless charging method and system based on radio frequency receiving and transmitting test and phase compensation retransmission. The method and the system could locate the apparatus to be charged precisely in unknown, random, and time-varying complex inhomogeneous environment, and realize directional transmission of electromagnetic power and focusing in a given area, having the feature of efficient energy transmission, stable transmission, little radiation to human body, and insensitive to external electromagnet interference.

A wireless charging technology theory based on radio frequency receiving and phase compensation retransmission, includes: transmitting a same frequency signal by a rechargeable battery in the embedded system, making multiple antennas system of the external charger receive the transmission phase delay data of the signal automatically. According to the reciprocity principle, when the same frequency signal is transmitted by the multiple antennas system of the charger, equal sized phase advance could be realized based on phase delay data obtained before. Thus, when the charging signals arrive at the rechargeable battery in the body, the field component of each antenna could stack in same phase, thereby realizing the focusing of field. When wireless energy transferring and wireless charging are not required, the embedded system keeps normal working which is related to the embedded system's function, while the apparatuses related to wireless receiving, transmitting and charging are in dormant state.

The invention adopts the following technical scheme:

Based on the propagation phase delay data received by the multiple antennas system of external charger from the same frequency signal transmitted by the embedded rechargeable battery, the external system transmits charging signal to the embedded system with the same frequency. Via the phase compensation when transmitting, focused electromagnetic field could be formed at the receiving antenna of the embedded system, realizing the efficient charging to the rechargeable battery of the embedded system. The concrete steps of the method comprise:

Step 1: transmitting a wake-up signal to an embedded system by an external system, making the embedded system being in a state to be charged.

Step 2: transmitting a test signal at a given frequency by the embedded system; receiving the test signal by the external system, and measuring the relative phases delay data of the signal received by each antenna units according to the reference phase of the same frequency reference signal of the external system.

Step 3: converting the external system to feeding state, setting the initial phases of a feed signal according to the phase data of the test signal received by each antenna units of the external system in Step 2, that is converting the obtained phase delay data to equal sized phase advance, realizing stacking in same phase by each signal when the same frequency signals transmitting by each antenna units of the external system arrive at a receiving antenna of the embedded system.

Step 4: feeding the transmitting multiple antennas system as the phase configuration in Step 3 by the external system, and the signals are transmitted to the receiving antenna of the embedded system by each antenna units, realizing in-phase stacking and the focus of field, and realizing effectively wireless charging to the embedded system.

Step 5: transmitting an acknowledgement signal by the embedded system after completing charging, and stopping charging after the acknowledgement signal is received by the external system.

Specifically, step 2-4 could be processed as many times as necessary.

For convenience of description, terms to be used are defined as follows:

Signals with the same frequency: test signals on a given frequency transmitting by the embedded system and charging signals emitted by the transmitting multiple antennas system of the external system are on the same frequency.

Power source: a power signal source device which could produce a given electromagnetic frequency, which supplies power electromagnetic signal to the transmitting antennas of the external system, and the feeding could be realized through coaxial cable, parallel double wire or microstrip line.

Phase control apparatus: an apparatus which could adjust the phase of power electromagnetic signal to a phase with a fixed phase difference compared to the reference signal, having the function of adjusting phase difference of power electromagnetic transmission signal arbitrarily.

Signal source: an apparatus which could generate a periodic signal at a given frequency and a given waveform period, supplying by DC power.

Referring to FIG. 1, as shown is a focused wireless charging apparatus based on radio frequency receiving and phase compensation retransmission, comprising: an embedded system 10 and an external system 20, wherein the embedded system comprises: a rechargeable battery 11, a signal source 12, a receiving antenna 13, a transmitting antenna 14; the external system comprises: a power source 21, a receiving multiple antennas system 23, a transmitting multiple antennas system 24; wherein the external system further comprises a phase control apparatus 22, and the receiving antenna and the transmitting antenna adopt a receiving system and a transmitting system with multiple antennas.

Moreover, the embedded system further comprises a receiving/transmitting control machine, and the receiving antenna and the transmitting antenna could be combined into one antenna, using a same antenna; the external system further comprises receiving/transmitting control machine as well, and the receiving multiple antennas system and the transmitting multiple antennas system could be combined into one, using a same multiple antennas system.

Moreover, each antenna unit of the receiving multiple antennas system and the transmitting multiple antennas system adopt microstrip patch antenna, microstrip slot antenna, element antenna, helical antenna or dielectric resonator antenna.

Moreover, the receiving multiple antennas system and the transmitting multiple antennas system of the external system could adopt one-dimensional linear antenna array, two-dimensional planar antenna array, surface antenna array or conformal antenna array of carrier conformal which needs to transmit energy to its internal.

The invention has the following beneficial effects:

1. The radiant electromagnetic power could focus (relatively concentrated) at the apparatus to be charged, with high energy transmission efficiency.

2. Without the need of obtaining the accurate location information of the inner apparatus to be charged in advance. As long as the apparatus is covered by beam of wake-up signal, then the apparatus is awakened and transmits a test signal, it could be located and focused automatically and electromagnetic power could be transmitted to the apparatus to be charged.

3. It is applicable for any mounting position (or current position when moving) or any complex electromagnetic transmission environment. This system could focus the electromagnetic energy on the battery to be charged automatically only if the system to be charged is not be shielded by metal shell completely.

4. The field strength and power density of electromagnetic is lesser in transmission areas except the battery to be charged, having lesser influence on the environment and human body.

5. Control circuit of the system is simple, which only needs a locking phase.

6. Antenna unit choosing is flexible, taking a unit form with mature technology is possible.

7. Distribution and arrangement of multiple antennas system are flexible, which is easy to miniaturize, with low profile and easy to be carrier conformal with embedded system to be charged.

8. No special material or special processing technology is needed, easy to manufacture, and with low cost.

9. With flexible implementation means, strong maneuverability, and easy to grasp and implement.

DETAILED DESCRIPTION OF THE PREFERRED EMBODIMENTS

Embodiment: transmitting energy wirelessly to an antenna unit in the chest by the multiple antennas system This invention will be described in further detail with reference to the drawings. It is understood that the embodiments and specific features of the embodiments of this invention are detailed illustrative of the technical proposal, but are not the limitation of the technical proposal of this invention. Embodiments and technical features of the embodiments of this invention may be combined with each other without conflict.

For convenience of explanation, in this embodiment, the receiving antenna and the transmitting antenna are combined into one, using a same antenna; receiving multiple antennas system and transmitting multiple antennas system are combined into one, using a same multiple antennas system.

Figure 3:
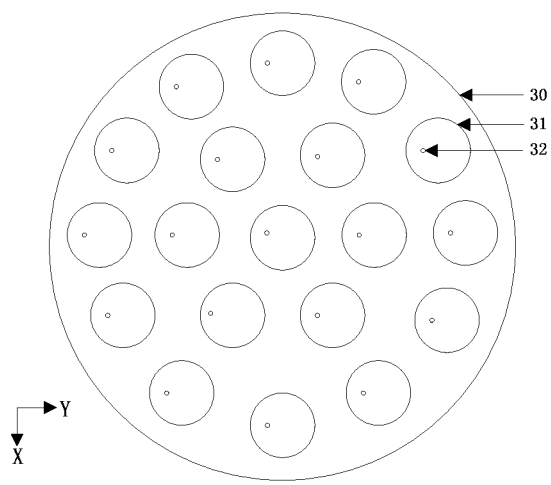
FIG. 3 is a transmitting multiple antennas system of an embodiment.
Figure 4:
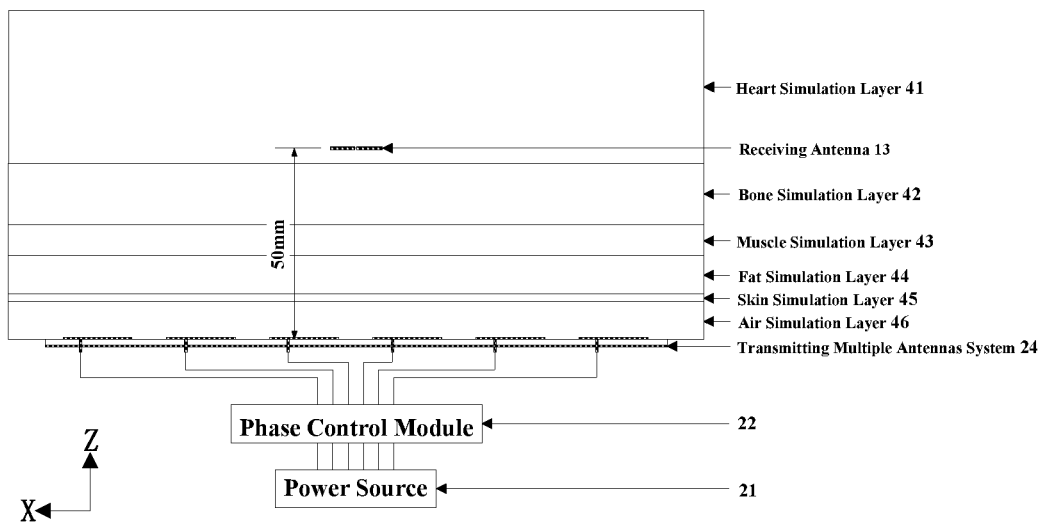
FIG. 4 is a model of adopting the transmitting multiple antennas system to transfer energy wirelessly to the receiving antenna in the chest in an embodiment.

Wireless energy transferring system shown in FIG. 4 is built utilizing the transmitting multiple antennas system shown in FIG. 3. The transmitting multiple antennas system is placed 10 mm above the tissue, and the multilayered depleted media is used to simulate chest tissue, wherein the heart simulation layer 41 is 40 mm thick, the bone simulation layer 42 is 16 mm thick, the muscle simulation layer 43 is 10 mm thick, the fat simulation layer 44 is 10 mm thick, the skin simulation layer 45 is 2 mm thick, and the air simulation layer 46 is 10 mm thick; the transmitting multiple antennas system 24 is shown in FIG. 3, the receiving antenna, which is vibrator antenna, is embedded in body, and is 50 mm far from the transmitting multiple antennas system.

Figure 1:
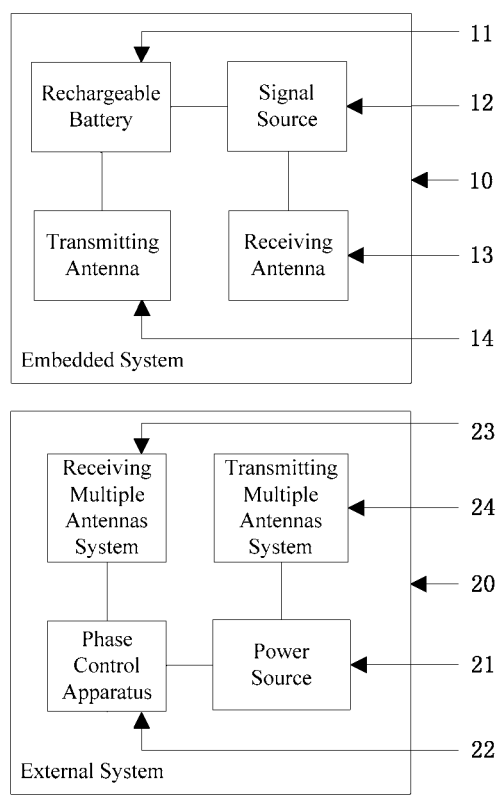
FIG. 1 is the system block diagram of this invention, comprising an embedded system and an external system.
Figure 2:
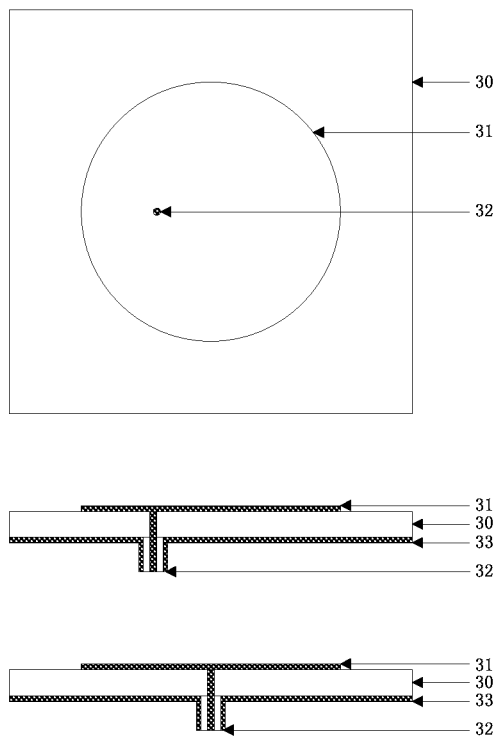
FIG. 2 is an antenna unit adopted by the transmitting multiple antennas system in an embodiment, and the antenna unit is a circular microstrip patch antenna; from top to bottom are vertical view, front view and side view respectively.

Firstly, a signal is transmitted by the receiving antenna embedded in body, and the signal is received by the transmitting multiple antennas system and is sent to the phase control apparatus, and the relative phases information of the signal obtained by each antenna unit (including antennas 30-33) of FIGS. 2 and 3 of the multiple antennas system is obtained by the phase control apparatus.

Then, the power source starts feeding, and the phase control apparatus locks the phase of the incoming signal respectively to the opposite value of the phases of the signal previously obtained from the antenna unit, then the signal is sent to the transmitting multiple antennas system, staring wireless energy transferring.

Figure 5:
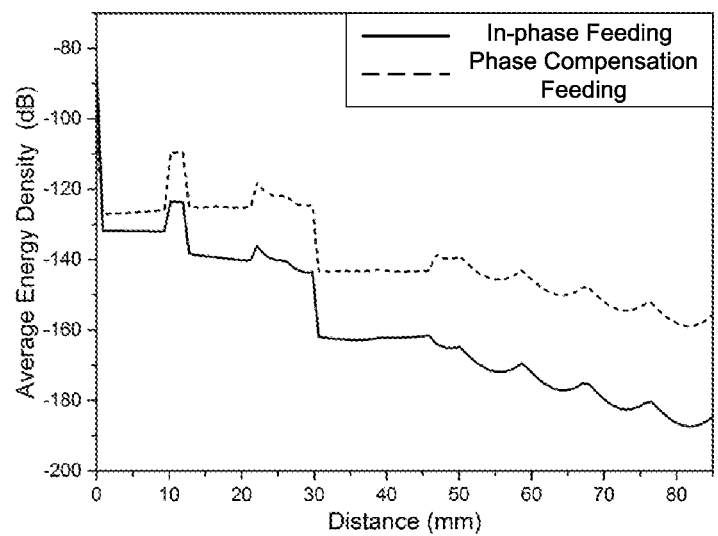
FIG. 5 is a change curve of the average energy density of electromagnetic field varies with the distance between the receiving antenna and the transmitting multiple antennas system when the transmitting multiple antennas system adopts equal phase feeding and the phase compensation method in an embodiment.

It could be seen from FIG. 5 that electromagnetic energy density on the transmission direction has obvious improvement compared to the conventional in-phase feeding after adopting the phase compensation feeding method of this invention to feed, and there is more than 20 dB improvement at 50 mm from the transmitting multiple antennas system.

Figure 6:
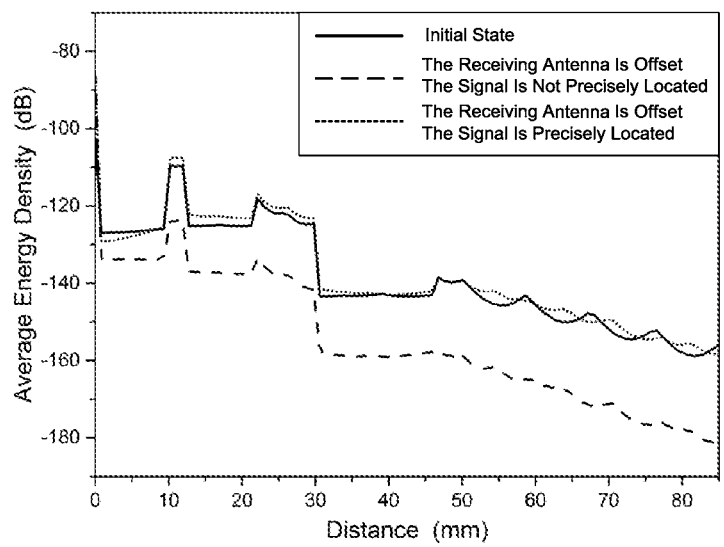
FIG. 6 is a change curve of average energy density of electromagnetic field varies with the distance between the receiving antenna and the transmitting multiple antennas system when the receiving antenna is offset with and without accurate location.

In order to illustrate the effect of the position offset of the receiving antenna on energy transmission, a change curve of average energy density of electromagnetic field varies with the distance between the receiving antenna and the transmitting multiple antennas system is drawn, as shown in FIG. 6. There are three curves in the figure, respectively: the initial state, which is the first case mentioned above; the receiving antenna is offset, but the signal transmitted by the transmitting multiple antennas system is not corrected, that is not precisely located and focused on the receiving antenna; and the receiving antenna is offset, and energy transmission is carried out after precisely locating and focusing by the method of this invention. It could be seen from the figure that when the receiving antenna is shifted, average electromagnetic energy density at the position 50 mm away from the transmitting multiple antennas system is decreased by 15 dB or more. While after the method of this invention is used for tracking, it is possible to achieve the initial state of the average electromagnetic energy density, that is achieving almost the same energy density as when the receiving antenna is not shifted, which proves the effectiveness of the method of this invention.

Above, the foregoing description of this invention is provided to personnel familiar to this field to facilitate their understanding and use of this invention. Various modifications to these embodiments would be apparent to personnel familiar with this technology without the need for creative work. Therefore, the present invention is not limited to methods and apparatuses described herein, but is consistent with the scope of the stated claim.

What is claimed:

1. A near field focused wireless charging method based on radio frequency receiving and phase compensation retransmission, comprising:

a first step of transmitting a wake-up signal to an embedded system by an external system, making the embedded system being in a state to be charged, wherein, the embedded system is embedded or implanted in a human body that comprises a time-varying complex inhomogeneous environment;

a second step of transmitting a test signal at a given frequency by the embedded system, receiving the test signal by the external system, and measuring relative phase delay data of the test signal received by each one of multiple antenna units according to a reference phase of a same frequency reference signal of the external system;

a third step of converting the external system to a feeding state, and for each antenna unit of the multiple antenna units of the external system, setting an initial phase of a feed signal of the antenna unit according to the phase delay data of the test signal received by the antenna unit in the second step, wherein the setting comprises converting the phase delay data of the test signal received by the antenna unit to an equal sized phase advance of the feed signal of the antenna unit, causing the initial phase of the feed signal of the antenna unit to be an opposite value of the phase of the test signal received by the antenna unit, and realizing stacking in same phase by each signal when same frequency signals transmitted by each one of the multiple antenna units of the external system arrive at a receiving antenna of the embedded system;

a fourth step of feeding a transmitting multiple antenna system according to a phase configuration in the third step by the external system, wherein signals are transmitted to the receiving antenna of the embedded system by each one of the multiple antenna units, realizing an in-phase stacking and a focus of field at the receiving antenna of the embedded system, and realizing wireless charging to the embedded system;

a fifth step of transmitting an acknowledgement signal by the embedded system after completing the wireless charging, and stopping the wireless charging after the acknowledgement signal is received by the external system.

2. The method according to claim 1, wherein the second step, the third step, and the fourth step are executed more than once according to a requirement.

3. A near field focused wireless charging apparatus based on radio frequency receiving and phase compensation retransmission, comprising:

an embedded system embedded or implanted in human body that comprises a time-varying complex inhomogeneous environment, comprising:
  a rechargeable battery;
  a signal source;
  a receiving antenna configured to receive a feed signal from the external system, realizing stacking in same phase by each feed signal when the feed signal transmitted by each one of multiple antenna units of the external system arrives at a receiving antenna of the embedded system; and
  a transmitting antenna configured to transmit a test signal at a given frequency, and to transmit an acknowledgement signal after completing the wireless charging, so as to stop the wireless charging after the acknowledgement signal is received by the external system;

an external system, comprising:
  a power source;
  a phase control apparatus configured to convert the external system to a feeding state, and for each antenna unit of the multiple antenna units of the external system, to set an initial phase of a feed signal of the antenna unit according to a phase delay data of the test signal received by the antenna unit, comprising converting the phase delay data of the test signal received by the antenna unit to an equal sized phase advance of the feed signal of the antenna unit, causing the initial phase of the feed signal of the antenna unit to be an opposite value of the phase of the test signal received by the antenna unit, and realizing stacking in same phase by each signal when the signals with the same frequency transmitted by each one of the multiple antenna units of the external system arrive at a receiving antenna of the embedded system;
  a receiving multiple antenna system configured to receive the test signal from the embedded system and to measure relative phase delay data of the test signal received by each of multiple antenna units according to a reference phase of a same frequency reference signal of the external system; and
  a transmitting multiple antenna system configured to transmit a wake-up signal to the embedded system to make the embedded system being in a state to be charged, and to transmit the feed signals converted by the phase control apparatus to the embedded system, wherein the feed signals are transmitted to the receiving antenna of the embedded system by each one of the multiple antenna units, realizing an in-phase stacking and a focus of field at the receiving antenna of the embedded system.

4. The apparatus according to claim 3, wherein the embedded system further comprises a first receiving/transmitting control machine, and the receiving antenna and the transmitting antenna are a same antenna,
wherein the external system further comprises a second receiving/transmitting control machine, and the receiving multiple antenna system and the transmitting multiple antenna system are a same multiple antenna system.

5. The apparatus according to claim 3, wherein each antenna unit of the receiving multiple antenna system and the transmitting multiple antenna system comprises a microstrip patch antenna, a microstrip slot antenna, an element antenna, a helical antenna, or a dielectric resonator antenna.

6. The apparatus according to claim 3, wherein the receiving multiple antenna system and the transmitting multiple antenna system of the external system comprise a one-dimensional linear antenna array, a two-dimensional planar antenna array, a surface antenna array, or a conformal antenna array of carrier conformal configured to transmit energy to its internal.

* * * * *